(12) United States Patent
Prevost

(10) Patent No.: US 12,024,912 B2
(45) Date of Patent: Jul. 2, 2024

(54) DEVICE FOR DEEP DECONTAMINATION OF PERSONS

(71) Applicant: UTILIS, Ennery (FR)

(72) Inventor: Philippe Prevost, Metz (FR)

(73) Assignee: Utilis, Ennery (FR)

( * ) Notice: Subject to any disclaimer, the term of this patent is extended or adjusted under 35 U.S.C. 154(b) by 208 days.

(21) Appl. No.: 17/596,713

(22) PCT Filed: Jun. 16, 2020

(86) PCT No.: PCT/IB2020/055607
§ 371 (c)(1),
(2) Date: Dec. 16, 2021

(87) PCT Pub. No.: WO2020/254953
PCT Pub. Date: Dec. 24, 2020

(65) Prior Publication Data
US 2022/0316226 A1 Oct. 6, 2022

(30) Foreign Application Priority Data

Jun. 21, 2019 (FR) .................................. FR1906702

(51) Int. Cl.
| | |
|---|---|
| *E04H 1/12* | (2006.01) |
| *A61L 2/00* | (2006.01) |
| *A61L 2/18* | (2006.01) |
| *B60P 3/00* | (2006.01) |
| *E04H 15/12* | (2006.01) |

(52) U.S. Cl.
CPC .......... *E04H 1/1277* (2013.01); *A61L 2/0088* (2013.01); *A61L 2/18* (2013.01); *B60P 3/005* (2013.01); *A61L 2202/11* (2013.01); *A61L 2202/122* (2013.01); *A61L 2202/15* (2013.01); *A61L 2202/16* (2013.01); *A61L 2202/17* (2013.01); *E04H 15/12* (2013.01)

(58) Field of Classification Search
CPC ..... E04H 1/1277; E04H 15/12; A61L 2/0088; A61L 2/18; A61L 2202/11; A61L 2202/122; A61L 2202/15; A61L 2202/16; A61L 2202/17; B60P 3/005
See application file for complete search history.

(56) References Cited

U.S. PATENT DOCUMENTS 4,706,551 A * 11/1987 Schofield .............. E04G 21/243
135/900
5,706,846 A * 1/1998 Sutton .................... A62B 31/00
135/900

(Continued)

*Primary Examiner* — Christine J Skubinna
(74) *Attorney, Agent, or Firm* — Colson Law Group, PLLC

(57) ABSTRACT

The present invention relates to a device for decontaminating persons, having a container having at least one decontamination shower, the container having at least one panel defined in an opening in one of the vertical walls of the container, the panel being mounted to pivot around a horizontal hinge which joins an upper edge of the panel to the container so as to be movable between a first position in which the panel extends substantially vertically and closes off the opening, and a second position in which the panel extends substantially horizontally and forms a ceiling covering a sheltered surface. The decontamination device also includes walls capable of closing off the sheltered surface to form at least one portion of the decontamination device.

14 Claims, 4 Drawing Sheets

(56) References Cited

U.S. PATENT DOCUMENTS

| | | | | |
|---|---|---|---|---|
| 5,833,294 A | * | 11/1998 | Williams | B60S 5/00 296/24.32 |
| 6,983,493 B1 | * | 1/2006 | Shaumyan | A47K 17/022 4/254 |
| 8,637,842 B2 | * | 1/2014 | Case, III | G21F 9/001 4/596 |
| 8,650,806 B1 | * | 2/2014 | Condie | E04H 1/1205 52/79.5 |

* cited by examiner

[Fig.1]
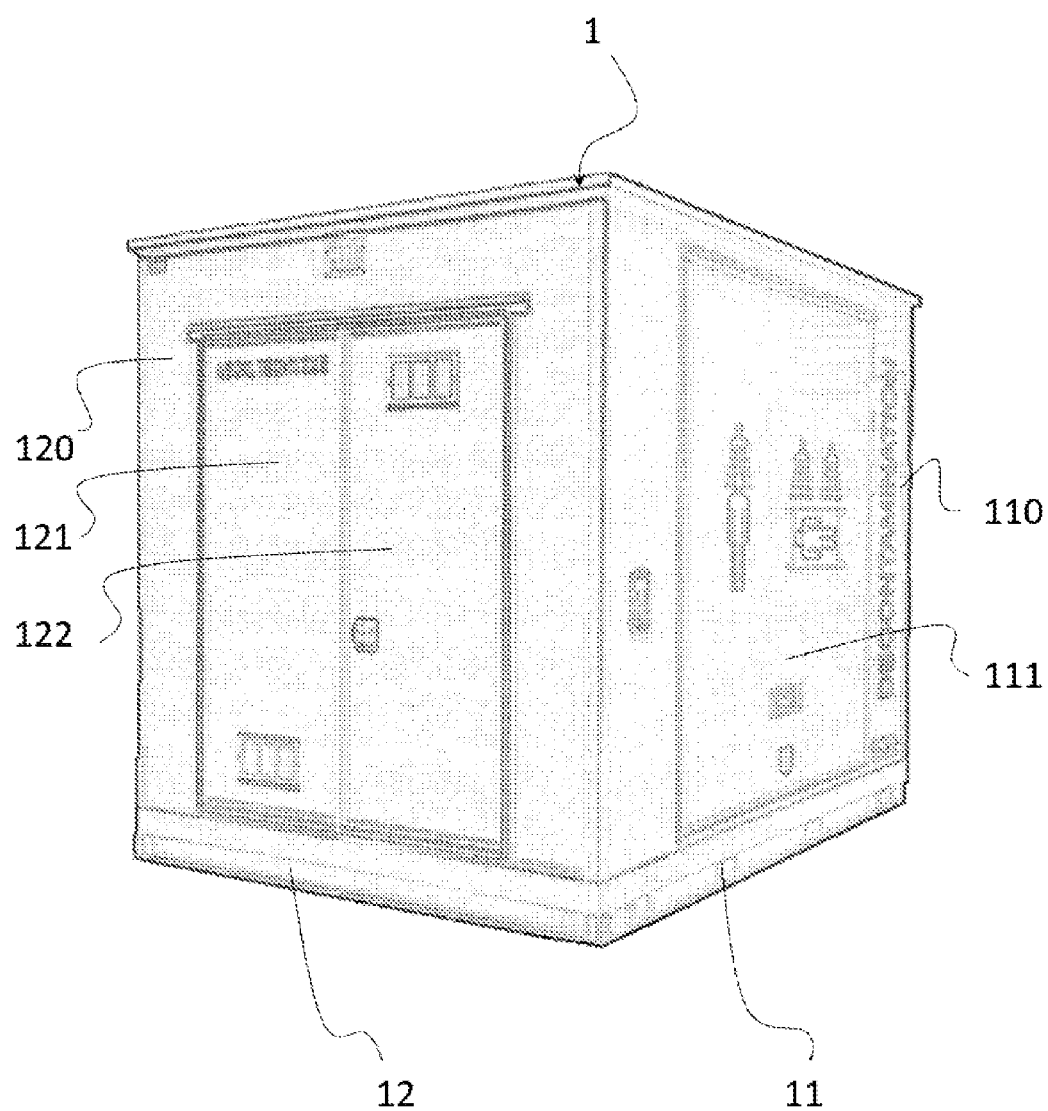

[Fig.2]
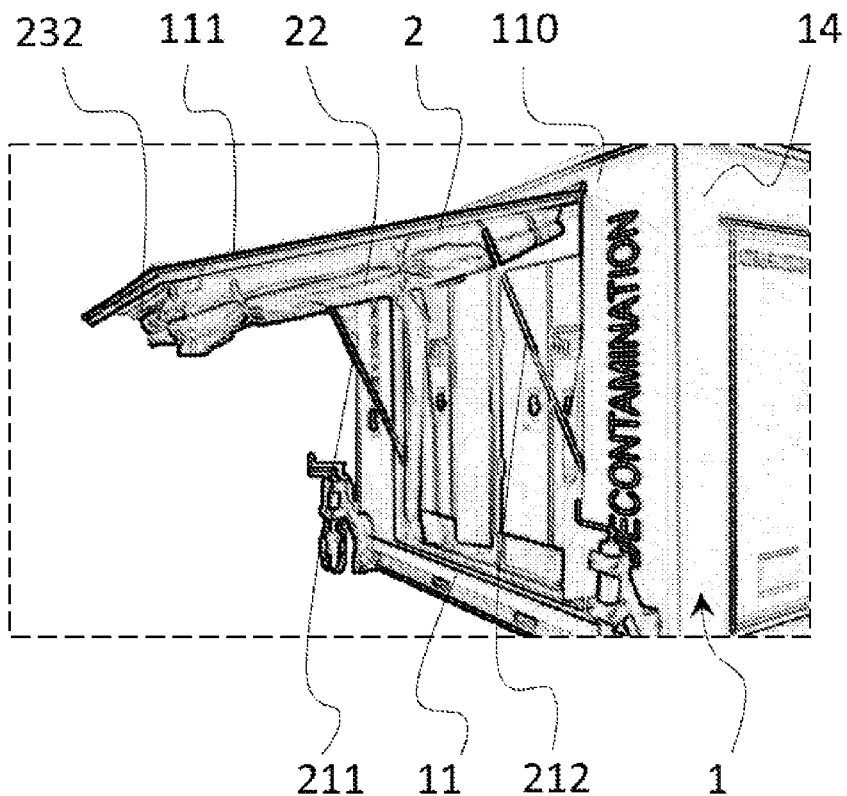
[Fig.3]
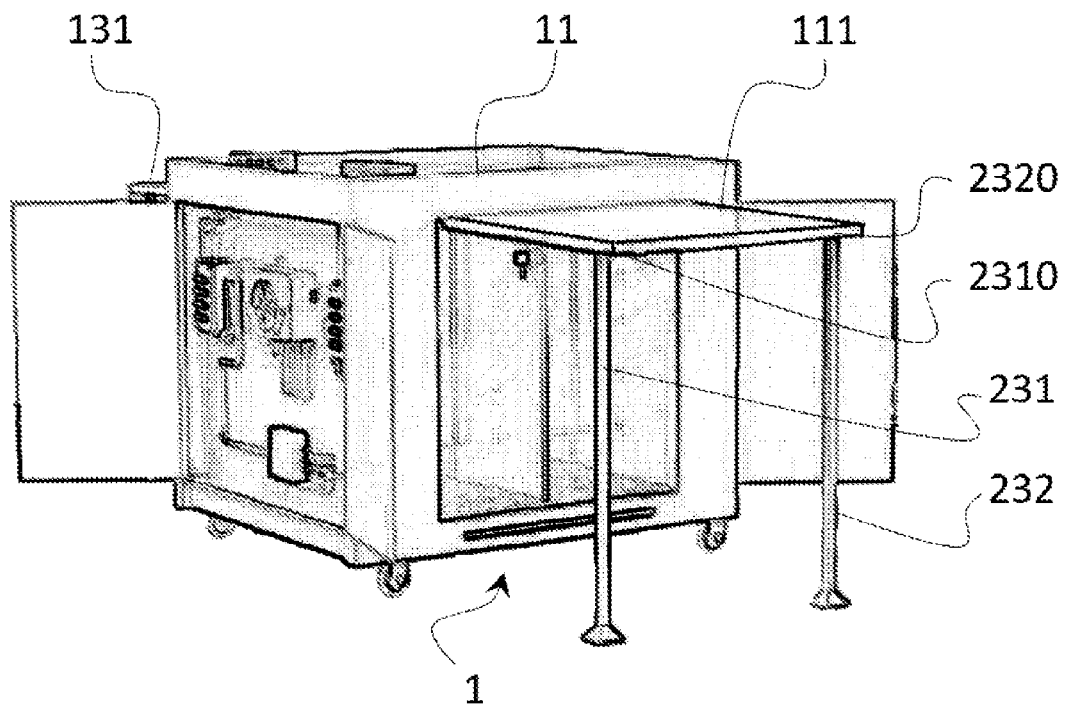

[Fig.4]
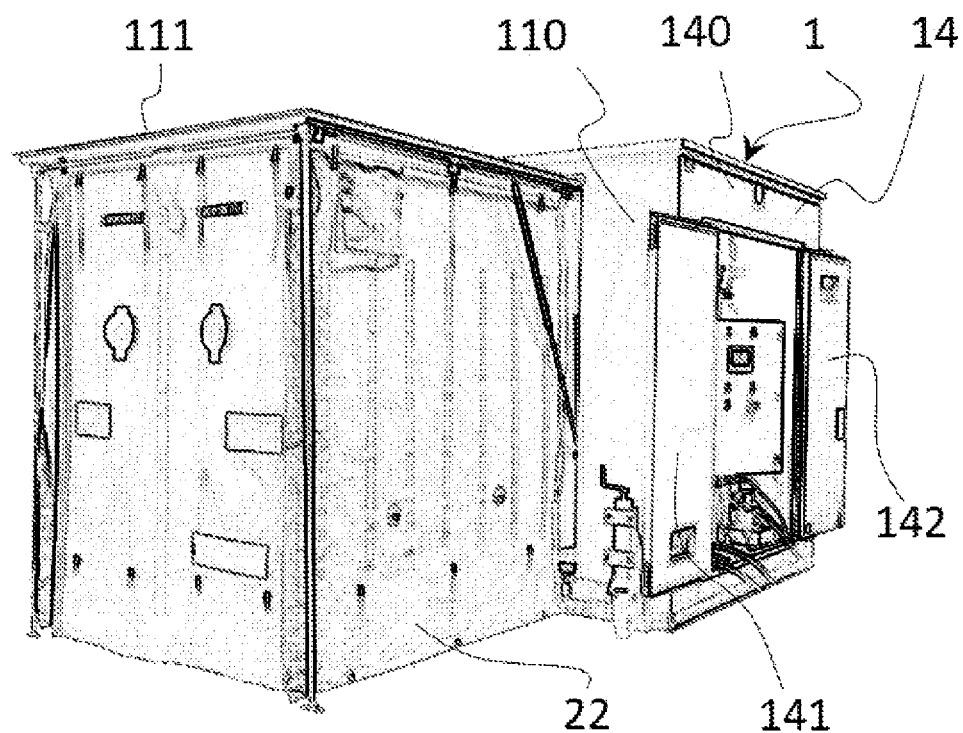
[Fig.5]
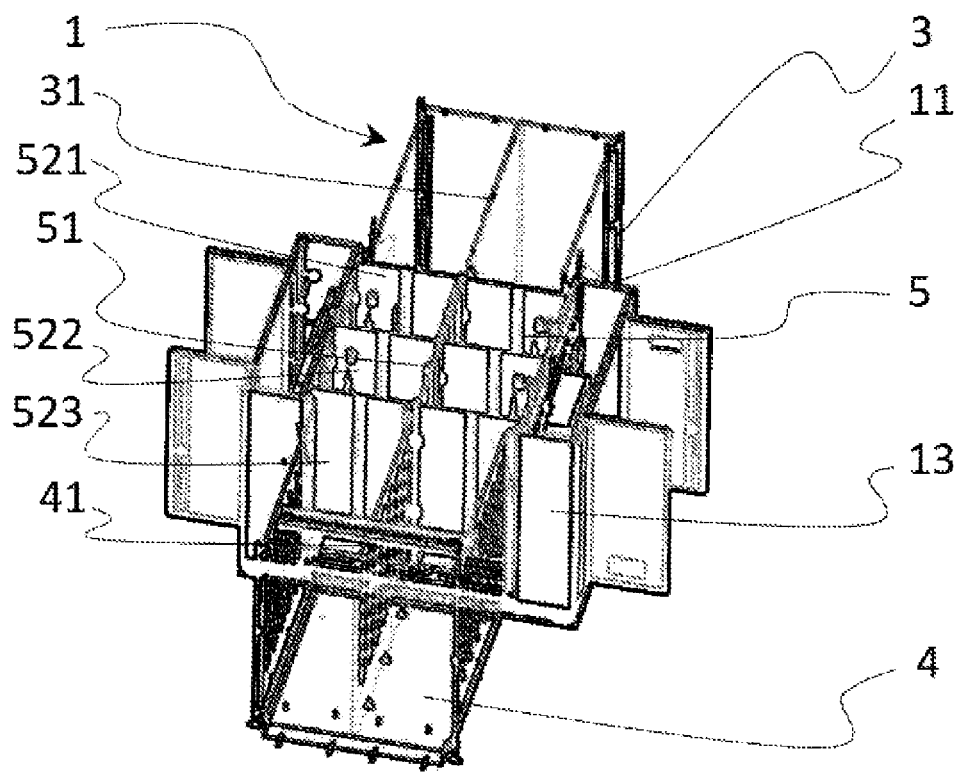

[Fig.6]
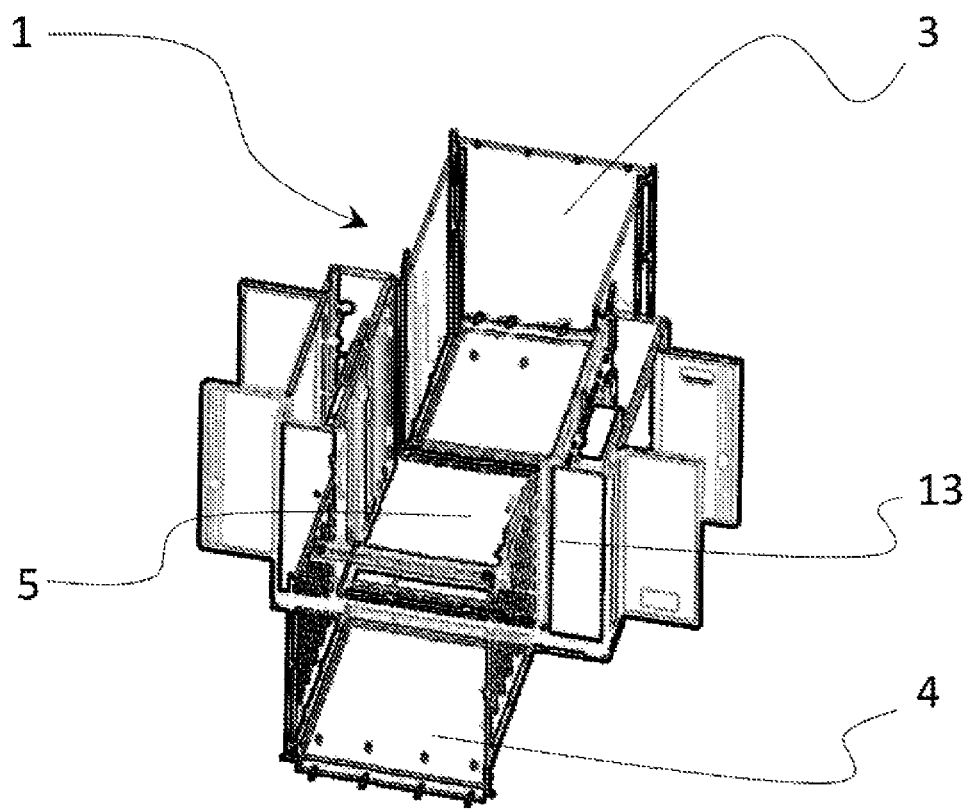

DEVICE FOR DEEP DECONTAMINATION OF PERSONS

FIELD OF THE INVENTION

The present invention relates to the field of decontamination of persons who have been exposed to contaminants.

In particular, the present invention relates to a device capable of providing deep decontamination of persons.

PRIOR ART

In the event of an industrial or environmental accident, or in the event of a military or terrorist attack involving the dispersion of contaminants, especially of radioactive, bacterial or chemical type, it may be necessary to decontaminate, as quickly as possible, persons who have come into contact with said contaminants.

Such decontamination may begin with a primary decontamination or emergency decontamination, which is implemented as quickly as possible after the contamination, as close as possible to the site of the contamination. The goal of this emergency decontamination is to reduce contamination on victims, and to limit as far as possible the transfer of contaminants which may spread the contamination.

Secondary decontamination, or deep decontamination, may be implemented after the emergency decontamination. It aims to eliminate the contaminants still present on the surface of the body which may be removed by the mechanical action of water. It involves implementing precise steps including undressing, intended to destroy contaminated clothing, decontamination cleaning, rinsing, drying by wiping, followed by checking for the absence of residual contamination. These different steps must be carried out according to a particular protocol which can only be effectively implemented with special equipment designed for this function.

In order to be effective, such devices for deep decontamination of persons must be deployed as close as possible to the contamination zone, very quickly after the occurrence of said contamination. It is therefore advantageous for these devices to be readily transportable, in order to be deployed at the desired location. However, it appears that transportable devices often require a relatively long installation time before they are operational.

There is therefore a need for a device for decontamination of persons which can be both effectively transported and implemented in a very short period of time, for example after the transport thereof.

AIMS OF THE INVENTION

The aim of the present invention is to overcome the disadvantages of the prior art.

In particular, one of the aims of the invention is to propose a device for deep decontamination of persons which has dimensions making it suitable for easy transportation.

Another aim of the invention is to propose such a device for decontamination of persons which can be implemented very quickly when required.

Another aim of the invention is to propose such a device for decontamination of persons which can be implemented while requiring very little equipment or resources external to the device itself.

Another aim of the invention is to propose such a device for decontamination of persons which can be implemented and utilized by a limited number of operators.

DISCLOSURE OF THE INVENTION

These aims and others which will become more clearly apparent hereinafter are achieved by means of a device for deep decontamination of persons which comprises, according to the invention, a container having at least one decontamination shower, the container having at least one panel defined in an opening in one of the vertical walls of the container, the panel being mounted to pivot around a horizontal hinge which joins an upper edge of the panel to the container so as to be movable between a first position in which the panel extends substantially vertically and closes off the opening, and a second position in which the panel extends substantially horizontally and forms a ceiling covering a sheltered surface, the decontamination device comprising walls capable of closing off the sheltered surface to form at least one portion of the decontamination device.

In the first position of the panel, which is also referred to as the closed position or vertical position, the decontamination device is in its closed configuration wherein it is compact and occupies a relatively small volume. The container shape thereof enables it to be stored and transported relatively easily, using standard means for storing and transporting containers.

If it is necessary to use it, the decontamination device can be deployed very quickly into its deployed configuration, the panel being able to pass into its second position, which is also referred to as deployed position or horizontal position. In this position, the panel covers an additional space, forming a portion which is closed off by the walls, which makes it possible to carry out the decontamination in a larger volume than the volume of the container containing the decontamination device.

Advantageously, the walls consist of canvas sheets fixed, at one edge thereof, close to at least one of the edges of the panel, so as to be deployed by gravity when the panel is in the second position, the canvas sheets being dimensioned so as to extend from the panel to the ground on which the container is placed, in the second position.

Such walls may be stowed very easily and deployed quickly after the panel has passed into the second position thereof.

Advantageously, at least one of the canvas sheets has means for attachment to an edge of the opening of the container.

Advantageously, the canvas sheets are attached over the whole length of the edges of the panel which do not carry the hinge.

Advantageously, actuating pistons are mounted between the container and the panel, which are able to participate in the movement of the panel from the first position thereof to the second position thereof.

Such actuating pistons make the handling of the panel very easy, and enable the quick and easy implementation of the decontamination device.

Advantageously, the device for decontamination of persons comprises feet able to extend vertically, when the panel is in the second position, between a position of the panel remote from the container and the ground.

Advantageously, at least one of the feet is attached to the panel via a pivot link.

Advantageously, at least one of the feet has an adjustable length.

Advantageously, the device for decontamination of persons comprises illumination means attached to said panels.

Advantageously, the container is equipped with wheels.

Advantageously, the container has two panels, defined respectively in openings in two opposite vertical walls of the container.

Advantageously, the container comprises at least two decontamination showers aligned between the openings.

Advantageously, the container comprises doors separating the showers from one another, and doors separating each of the showers from the surfaces sheltered by the panels.

Advantageously, the device for decontamination of persons comprises removable partitions able to form at least two corridors, each of the corridors passing through the container, each of the openings, and the spaces sheltered by the panels, the container comprising at least two decontamination showers aligned in each of the corridors.

Advantageously, the device for decontamination of persons comprises a device for recovering water from the showers.

LIST OF FIGURES

The invention will be better understood upon reading the following description of preferred embodiments, given by way of simple figurative and non-limiting example and accompanied by the figures, in which:

FIG. 1 is a perspective view of a device for decontamination of persons according to one embodiment of the invention, in the closed configuration thereof, making it suitable for transport;

FIG. 2 is a perspective view of the decontamination device of FIG. 1, during the opening of one of the movable panels thereof;

FIG. 3 is a perspective view of the decontamination device of FIG. 1, wherein the movable panels are placed in the horizontal position;

FIG. 4 is a perspective view of the decontamination device of FIG. 1, in a deployed configuration;

FIG. 5 is a cut-away perspective view of the decontamination device of FIG. 1 in a deployed configuration, making it possible to see the interior arrangement of this device;

FIG. 6 is a cut-away perspective view of the decontamination device of FIG. 1, in another deployed configuration, making it possible to see the interior arrangement of this device.

DETAILED DESCRIPTION OF EMBODIMENTS OF THE INVENTION

FIG. 1 shows a container 1 constituting a device for deep decontamination of persons, or device for decontamination of persons, according to one embodiment of the invention. This container 1 is a parallelepipedal metal box, the dimensions of which may advantageously be standardized in order to facilitate the transport thereof, for example on a truck.

FIG. 1 shows one of the longest lateral faces of the container, hereinafter referred to as front face 11 of this container. This front face 11 is formed by a fixed panel 110 defining an opening in which a movable panel 111 is placed. The fixed panel 110 surrounds the movable panel 111, on the sides and above the latter.

FIG. 1 also shows one of the shortest lateral faces of the container 2, hereinafter referred to as left lateral face 12. This left lateral face 12 consists of a fixed panel 120 defining an opening in which door panels 121 and 122 are placed. The fixed panel 120 surrounds the door panels 121 and 122 one the sides and above these door panels.

The container 1 also has a rear face 13, opposite the front face 11 thereof, which can be seen in particular in FIG. 5.

This rear face consists of a fixed panel 130 defining an opening in which a movable panel 131 is placed, the fixed panel and the movable panel being arranged substantially as on the front face 11.

The container 1 finally comprises a right lateral face 14, located opposite the left lateral face 12 and consisting of a fixed panel 140 defining an opening in which door panels 141 and 142 are placed, arranged substantially as on the left lateral face. This right lateral face 14 can be seen in particular in FIG. 4.

Advantageously, the movable panel 111 can pivot about a horizontal hinge placed between the upper horizontal edge of the movable panel 111 and the fixed panel 110. The pivoting of this movable panel 111 about this hinge makes it possible to open the front face of the container 1, as shown in FIG. 2.

In FIG. 2, the movable panel 111 is shown in an intermediate position between the closed vertical position thereof, shown in FIG. 1, in which it closes off the opening of the front face 11, and the deployed horizontal position thereof. It can be seen in this FIG. 2 that the lateral edges of the movable panel 111 are connected to the fixed panel 110 by gas actuating pistons 211 and 212. These gas actuating pistons are advantageously dimensioned to assist in at least some of the opening movement of the movable panel 111 from the vertical position thereof, shown in FIG. 1, to the horizontal position thereof, shown in FIG. 3.

The inner face 2 of the movable panel 111, which is inside the container 1 when the movable panel 111 is closed, advantageously carries two pivoting and adjustable feet 231 and 232 which are, in the configuration depicted in FIG. 2, stowed along the edge of the movable panel 111 opposite the hinge.

When the movable panel 111 is placed in the horizontal position, as shown in FIG. 3, these two feet 231 and 232 can each pivot about a pivot, respectively 2310 and 2320, connecting one end of the foot, respectively 231 and 232, to the inner face 2 of the movable panel 111, close to the two corners of this movable panel 111 which are remote from the hinge. When the movable panel 111 is horizontal, the feet 231 and 232 can thus be placed in a vertical position as shown in FIG. 3. The length of these feet 231 and 232 is moreover adjustable, such that these feet can bear against the ground to hold the movable panel 111 in the horizontal position thereof. In this position, shown in FIG. 3, the movable panel 111 forms a ceiling, sheltering the surface which it overhangs.

Moreover, the inner face 2 also carries rolled-up canvas sheets 22 which are attached along the three edges of the movable panel 111 which do not carry the hinge. Advantageously, one edge of each of these canvas sheets is attached to the inner face 2.

When the movable panel 111 is in the horizontal position thereof, the canvas sheets 22 carried by the inner face 2 thereof can be unrolled, with one of their edges remaining attached to this inner face 2. FIG. 4 shows the container 1 from which these canvas sheets 22 have been unrolled. These canvas sheets 22 then extend from the movable panel 111 to the ground. They may advantageously be assembled with one another and with the edges of the fixed panel 110 so as to enclose the space covered by the movable panel 111.

In this configuration, shown in FIG. 4, the space covered by the movable panel 111 thus forms a closed and covered portion of the device for decontamination of persons. Advantageously, an opening may be provided in one of the canvas sheets 24 forming this portion, for example on the canvas sheet placed opposite the opening of the container 1, in order to form an entry door into this portion.

In the device for decontamination of persons according to the embodiment shown, this portion covered by the movable panel 111 constitutes an entry vestibule 3. In a decontamination process, this entry vestibule 3 can be used for undressing contaminated persons and containment of contaminated clothing.

Advantageously, a floor mat can be placed on the ground of this entry vestibule 3. Moreover, the inner face 2 of the movable panel 111 may carry illumination, consisting for example of LED lamps, which form a ceiling light which illuminates the decontamination vestibule 3.

Advantageously, the movable panel 131 of the rear face 13 can be deployed in the same manner as the movable panel 111, and is equipped substantially identically in order to be able to shelter and close off a zone forming a portion referred to hereinafter as exit vestibule 4. In a decontamination process, this entry vestibule can be used for drying, checking for the absence of contaminants on persons who have been decontaminated, and dressing with uncontaminated clothing.

FIG. 5 is a cut-away perspective view of the decontamination device when the entry vestibule 3 and the exit vestibule 4 are installed, wherein the ceilings have not been shown in order to make the interior arrangement of this device visible. Inside the container 1, the zone located between the entry vestibule 3 and the exit vestibule 4 is referred to as the cleaning zone 5. This cleaning zone 5 is open to the entry 3 and exit 4 vestibules, the movable panels 110 and 131 revealing openings in the front 11 and rear 13 faces when they are in the horizontal position thereof.

The entry vestibule 3, the cleaning zone 5 and the exit vestibule 4 are, in the embodiment shown in FIG. 5, equipped with movable partitions, and doors. Thus, separating partitions 31 in the entry vestibule 3, 51 in the cleaning zone 5 and 41 in the exit vestibule 4 each separate these spaces into two substantially equal parts. These separating partitions make it possible to define, through the mobile decontamination device, two discrete decontamination corridors, each passing successively through the entry vestibule 3, the cleaning zone 5 and the exit vestibule 4.

These separating partitions can for example be formed by canvas sheets which, in the entry vestibule 3 and the exit vestibule 4, can be carried by the movable panels 111 and 131 and extend to the ground in order to close off the spaces, or on the contrary be rolled up in order to do away with the partitioning. In the cleaning zone 5, these canvas sheets can be attached to the ceiling of the container 1 and/or to lateral uprights.

In the configuration shown in FIG. 5, the cleaning zone 5 also comprises swing doors separating different spaces. In each of the two decontamination corridors, swing doors 521 thus separate the entry vestibule 3 from the cleaning zone 5, with swing doors 523 separating the cleaning zone 5 from the exit vestibule 4. Moreover, swing doors 522 separate the cleaning zone 5 into two spaces.

Each of these spaces in the cleaning zone 5 is equipped with a shower head which can be attached to supports close to the ceiling. In a decontamination process, the shower located in the space located close to the entry vestibule can be used for the decontamination cleaning, and the shower in the space located close to the exit vestibule can be used for rinsing.

FIG. 6 is a cut-away perspective view of the decontamination device of FIG. 1, in another deployed configuration, making it possible to see the interior arrangement of this device. In this configuration, the separating partitions and the swing doors are removed in order to define, in the mobile decontamination device, a single, larger decontamination circuit, enabling for example the passage of a person lying on a stretcher, carried and decontaminated by caregivers.

This single decontamination circuit passes successively through the entry vestibule 3, the cleaning zone 5 and the exit vestibule 4. In this configuration, the four shower heads of the cleaning zone 5 can be detached from their supports to be used by the caregivers in order to carry out the decontamination of the person lying on the stretcher.

FIGS. 5 and 6 also show two lateral compartments 61 and 62 in the container 1. The compartment 61, which can be accessed via the door panels 141 and 142 of the right lateral face 14, is a storage compartment. The compartment 62, which can be accessed via the door panels 121 and 122 of the left lateral face 12, contains the controls for the hydraulic, electric and electronic operating circuits for the decontamination device.

Among the hydraulic equipment contained in the decontamination device, a clean water supply circuit is advantageously provided, enabling the supply to the shower heads. This circuit may comprise, in some embodiments, a water heating system. It may advantageously be connected to the water supply network or to a mobile tank.

In the floor of the cleaning zone 5, a device for collecting wastewater is also provided, which can be connected to a reservoir for collecting potentially contaminated wastewater. This reservoir may for example be a flexible reservoir placed outside the container 1.

The electric and electronic equipment may comprise means for illuminating different parts of the decontamination equipment, and light signaling systems with the aim of automatically indicating to users, in the configuration of FIG. 5, when they should pass through one of the swing doors within the context of a decontamination process. This signaling system, associated with a system for detecting the opening of the swing doors, enables the device to perform the rapid decontamination of numerous persons.

The device for decontamination of persons can also, where required, contain or be associated with equipment for heating by blowing hot air.

The decontamination equipment can be supplied with electricity by connection to an electric grid or to a device which produces electricity, such as a generator.

When the decontamination device is stowed, as shown in FIG. 1, it is entirely contained within the parallelepipedal container 1 and can be easily transported, for example on a truck. In order to facilitate the transport thereof, its base can provide openings intended for the introduction of the carrying forks of a pallet transporter. The ceiling of the container 1 can also be equipped with hooks enabling the attachment thereof in order to be raised by a crane. Finally, the container 1 can also be equipped with wheels, which may be removable, close to the four corners thereof. Such wheels make it possible to facilitate the transport thereof over short distances.

The invention claimed is:

1. A device for deep decontamination of persons, comprising a container having at least one decontamination shower, said container having at least one panel, defined in an opening in one of the vertical walls of said container,
    wherein said panel is mounted to pivot around a horizontal hinge which joins an upper edge of said panel to said container so as to be movable between:
        a first position in which said panel extends substantially vertically and closes off said opening; and, a second position in which said panel extends substantially horizontally and forms a ceiling covering a sheltered surface; and, in that said decontamination device comprises walls capable of closing off said sheltered surface to form at least one portion of said decontamination device, said walls consist of canvas sheets fixed, at one edge thereof, to at least one of the edges of said panel, so as to be deployed by gravity when the panel is in said second position, said canvas sheets being dimensioned so as to extend from said panel to the ground on which the container is placed, in said second position.

2. The device for decontamination of persons according to claim 1, wherein at least one of said canvas sheets has means for attachment to an edge of said opening of the container.

3. The device for decontamination of persons according to claim 1, wherein said canvas sheets are attached over the whole length of the edges of said panel which do not carry said hinge.

4. The device for decontamination of persons according to claim 1, wherein actuating pistons are mounted between said container and said panel, said actuating pistons operatively arranged to assist in the movement of the panel from the first position thereof to the second position thereof.

5. The device for decontamination of persons according to claim 1, further comprising feet able to extend vertically, when said panel is in said second position, between a portion of said panel remote from said container and the ground.

6. The device for decontamination of persons according to claim 5, wherein at least one of said feet is attached to said panel via a pivot link.

7. The device for decontamination of persons according to claim 5, wherein at least one of said feet has an adjustable length.

8. The device for decontamination of persons according to claim 1 further comprising illumination means attached to said panels.

9. The device for decontamination of persons according to claim 1, wherein said container is equipped with wheels.

10. The device for decontamination of persons according to claim 1, wherein said container has two of said panels, defined respectively in openings in two opposite vertical walls of said container.

11. The device for decontamination of persons according to claim 10, wherein said container comprises at least two decontamination showers aligned between said openings.

12. The device for decontamination of persons according to claim 11, wherein said container comprises doors separating said showers from one another, and doors separating each of said showers from the surfaces sheltered by said panels.

13. The device for decontamination of persons according to claim 10 further comprising removable partitions able to form at least two corridors, each of said corridors passing through said container, each of said openings, and the spaces sheltered by said panels, said container comprising at least two decontamination showers aligned in each of said corridors.

14. The device for decontamination of persons according to claim 1 further comprising a device for recovering water from said at least one decontamination shower.

* * * * *